(12) United States Patent
Schulz et al.

(10) Patent No.: US 7,197,198 B2
(45) Date of Patent: Mar. 27, 2007

(54) BIOSENSOR SUBSTRATE STRUCTURE FOR REDUCING THE EFFECTS OF OPTICAL INTERFERENCE

(75) Inventors: Stephen C. Schulz, Lee, NH (US); Brian T. Cunningham, Champaign, IL (US)

(73) Assignee: SRU Biosystems, Inc., Woburn, MA (US)

( * ) Notice: Subject to any disclaimer, the term of this patent is extended or adjusted under 35 U.S.C. 154(b) by 0 days.

(21) Appl. No.: 11/207,491

(22) Filed: Aug. 18, 2005

(65) Prior Publication Data

US 2006/0291766 A1 Dec. 28, 2006

Related U.S. Application Data

(60) Provisional application No. 60/693,653, filed on Jun. 23, 2005.

(51) Int. Cl.
*G02B 6/00* (2006.01)
(52) U.S. Cl. .......................................... 385/12; 385/13
(58) Field of Classification Search ............ 385/12–13; 435/288.7
See application file for complete search history.

(56) References Cited

U.S. PATENT DOCUMENTS

| | | | | |
|---|---|---|---|---|
| 3,693,025 | A * | 9/1972 | Brunton | 250/340 |
| 5,332,643 | A * | 7/1994 | Harada et al. | 430/127 |
| 5,401,600 | A * | 3/1995 | Aizawa et al. | 430/65 |
| 5,654,118 | A * | 8/1997 | Yuh et al. | 430/65 |
| 6,741,307 | B2 * | 5/2004 | Matsunaga et al. | 349/112 |
| 6,861,121 | B2 * | 3/2005 | Matsunaga et al. | 428/141 |
| 2002/0127565 | A1 | 9/2002 | Cunningham et al. | 435/6 |
| 2003/0017581 | A1 | 1/2003 | Li et al. | 435/287.2 |
| 2003/0027327 | A1 | 2/2003 | Cunningham et al. | 435/287.2 |
| 2003/0032039 | A1 | 2/2003 | Cunningham et al. | 435/6 |
| 2003/0059855 | A1 | 3/2003 | Cunningham et al. | 435/7.9 |
| 2003/0077660 | A1 | 4/2003 | Pien et al. | 435/7.1 |

FOREIGN PATENT DOCUMENTS

JP 04233546 A * 8/1992

OTHER PUBLICATIONS

Cunningham, B.T., P. Li, B. Lin, and J. Pepper, *Colorimetric resonant reflection as a direct biochemical assay technique*. Sensors and Actuators B, 2002. 81: p. 316-328.

(Continued)

*Primary Examiner*—Quyen Leung
(74) *Attorney, Agent, or Firm*—McDonnell Boehnen Hulbert & Berghoff LLP

(57) ABSTRACT

A biosensor substrate structure is provided that eliminates the effects of optical interference of light reflected from a substrate/air interface with light reflected by the biosensor's active surface by incorporating a roughened or "non-specular" surface on the lower surface of the substrate opposite the grating. One can generate a useful non-specular or "anti-interference" surface in a number of ways in accordance with this disclosure, including (1) by adding a coating of optically diffuse material, such as UV cured acrylate, to the sensor substrate, (2) etching or otherwise roughening the surface of the sensor substrate, or (3) applying a grating structure to the surface.

32 Claims, 2 Drawing Sheets

OTHER PUBLICATIONS

Cunningham, B.T., J. Qiu, P. Li, J. Pepper, and B. Hugh, *A plastic colorimetric resonant optical biosensor for multiparallel detection of label-free biochemical interactions*, Sensors and Actuators B, 2002. 85: p. 219-226.

Haes, A.J. and R.P.V. Duyne, *A Nanoscale Optical Biosensor: Sensitivity and Selectivity of an Approach Based on the Localized Surface Plasmon Resonance Spectroscopy of Triangular Silver Nanoparticles*. Journal of the American Chemical Society, 2002. 124: p. 10596-10604.

Li, P., B. Lin, J. Gerstenmaier, and B.T. Cunningham, *A new method for label-free imaging of biomolecular interactions*. Sensors and Actuators B, 2003.

PCT International Search Report in PCT/US2006/14429, application of SRU Biosystems, Inc.; dated Sep. 20, 2006.

Written Opinion in PCT/US2006/14429, application of SRU Biosystems, Inc., dated Sep. 20, 2006.

* cited by examiner

BIOSENSOR SUBSTRATE STRUCTURE FOR REDUCING THE EFFECTS OF OPTICAL INTERFERENCE

CROSS-REFERENCE TO RELATED APPLICATION

This application claims priority benefits under 35 U.S.C. § 119(e) of U.S. Provisional application Ser. No. 60/693,653 filed Jun. 23, 2005, the entire content of which is incorporated by reference herein.

BACKGROUND

A. Field of the Invention

This invention relates generally to grating-based biochemical sensor devices, and methods of manufacture of such devices. Such devices are typically based on photonic crystal technology and are used for optical detection of the adsorption of a biological material, such as DNA, protein, viruses or cells, or chemicals, onto a surface of the device or within a volume of the device.

B. Description of Related Art

Grating-based biosensors represent a new class of optical devices that have been enabled by recent advances in semiconductor fabrication tools with the ability to accurately deposit and etch materials with precision less than 100 nm.

Several properties of photonic crystals make them ideal candidates for application as grating-type optical biosensors. First, the reflectance/transmittance behavior of a photonic crystal can be readily manipulated by the adsorption of biological material such as proteins, DNA, cells, virus particles, and bacteria. Each of these types of material has demonstrated the ability to alter the optical path length of light passing through them by virtue of their finite dielectric permittivity. Second, the reflected/transmitted spectra of photonic crystals can be extremely narrow, enabling high-resolution determination of shifts in their optical properties due to biochemical binding while using simple illumination and detection apparatus. Third, photonic crystal structures can be designed to highly localize electromagnetic field propagation, so that a single photonic crystal surface can be used to support, in parallel, the measurement of a large number of biochemical binding events without optical interference between neighboring regions within <3–5 microns. Finally, a wide range of materials and fabrication methods can be employed to build practical photonic crystal devices with high surface/volume ratios, and the capability for concentrating the electromagnetic field intensity in regions in contact with a biochemical test sample. The materials and fabrication methods can be selected to optimize high-volume manufacturing using plastic-based materials or high-sensitivity performance using semiconductor materials.

Representative examples of grating-type biosensors in the prior art are disclosed in Cunningham, B. T., P. Li, B. Lin, and J. Pepper, *Colorimetric resonant reflection as a direct biochemical assay technique.* Sensors and Actuators B, 2002. 81: p. 316–328; Cunningham, B.T., J. Qiu, P. Li, J. Pepper, and B. Hugh, *A plastic colorimetric resonant optical biosensor for multiparallel detection of label-free biochemical interactions,* Sensors and Actuators B, 2002. 85: p. 219–226; Haes, A. J. and R. P. V. Duyne, *A Nanoscale Optical Biosensor: Sensitivity and Selectivity of an Approach Based on the Localized Surface Plasmon Resonance Spectroscopy of Triangular Silver Nanoparticles.* Journal of the American Chemical Society, 2002. 124: p. 10596–10604.

The combined advantages of photonic crystal biosensors may not be exceeded by any other label-free biosensor technique. The development of highly sensitive, miniature, low cost, highly parallel biosensors and simple, miniature, and rugged readout instrumentation will enable biosensors to be applied in the fields of pharmaceutical discovery, diagnostic testing, environmental testing, and food safety in applications that have not been economically feasible in the past.

In order to adapt a photonic bandgap device to perform as a biosensor, some portion of the structure must be in contact with a liquid test sample. Biomolecules, cells, proteins, or other substances are introduced to the portion of the photonic crystal and adsorbed where the locally confined electromagnetic field intensity is greatest. As a result, the resonant coupling of light into the crystal is modified, and the reflected/transmitted output (i.e., peak wavelength) is tuned, i.e., shifted. The amount of shift in the reflected output is related to the amount of substance present on the sensor. The sensors are used in conjunction with an illumination and detection instrument that directs polarized light into the sensor and captures the reflected or transmitted light. The reflected or transmitted light is fed to a spectrometer that measures the shift in the peak wavelength.

The ability of photonic crystals to provide high quality factor (Q) resonant light coupling, high electromagnetic energy density, and tight optical confinement can also be exploited to produce highly sensitive biochemical sensors. Here, Q is a measure of the sharpness of the peak wavelength at the resonant frequency. Photonic crystal biosensors are designed to allow a liquid test sample to penetrate the periodic lattice, and to tune the resonant optical coupling condition through modification of the surface dielectric constant of the crystal through the attachment of biomolecules or cells. Due to the high Q of the resonance, and the strong interaction of coupled electromagnetic fields with surface-bound materials, several of the highest sensitivity biosensor devices reported are derived from photonic crystals. See the Cunningham et al. papers cited previously. Such devices have demonstrated the capability for detecting molecules with molecular weights less than 200 Daltons (Da) with high signal-to-noise margins, and for detecting individual cells. Because resonantly-coupled light within a photonic crystal can be effectively spatially confined, a photonic crystal surface is capable of supporting large numbers of simultaneous biochemical assays in an array format, where neighboring regions within ~10 μm of each other can be measured independently. See Li, P., B. Lin, J. Gerstenmaier, and B. T. Cunningham, *A new method for label-free imaging of biomolecular interactions.* Sensors and Actuators B, 2003.

There are many practical benefits for biosensors based on photonic crystal structures. Direct detection of biochemical and cellular binding without the use of a fluorophore, radioligand or secondary reporter removes experimental uncertainty induced by the effect of the label on molecular conformation, blocking of active binding epitopes, steric hindrance, inaccessibility of the labeling site, or the inability to find an appropriate label that functions equivalently for all molecules in an experiment. Label-free detection methods greatly simplify the time and effort required for assay development, while removing experimental artifacts from quenching, shelf life, and background fluorescence. Compared to other label-free optical biosensors, photonic crystals are easily queried by simply illuminating at normal incidence with a broadband light source (such as a light bulb or LED) and measuring shifts in the reflected color. The simple excitation/readout scheme enables low cost, miniature, robust systems that are suitable for use in laboratory instruments as well as portable handheld systems for point-of-care medical diagnostics and environmental monitoring. Because the photonic crystal itself consumes no power, the devices are easily embedded within a variety of liquid or gas sampling systems, or deployed in the context of an optical network where a single illumination/detection base station can track the status of thousands of sensors within a building. While photonic crystal biosensors can be fabricated using a wide variety of materials and methods, high sensitivity structures have been demonstrated using plastic-based processes that can be performed on continuous sheets of film. Plastic-based designs and manufacturing methods will enable photonic crystal biosensors to be used in applications where low cost/assay is required, that have not been previously economically feasible for other optical biosensors.

The assignee of the present invention has developed a photonic crystal biosensor and associated detection instrument. The sensor and detection instrument are described in the patent literature; see U.S. patent application publications U.S. Pat. Nos. 2003/0027327; 2002/0127565, 2003/0059855 and 2003/0032039. Methods for detection of a shift in the resonant peak wavelength are taught in U.S. Patent application publication 2003/0077660. The biosensor described in these references include 1- and 2-dimensional periodic structured surfaces applied to a continuous sheet of plastic film or substrate. The crystal resonant wavelength is determined by measuring the peak reflectivity at normal incidence with a spectrometer to obtain a wavelength resolution of 0.5 picometer. The resulting mass detection sensitivity of <1 $pg/mm^2$ (obtained without 3-dimensional hydrogel surface chemistry) has not been demonstrated by any other commercially available biosensor.

A fundamental advantage of the biosensor devices described in the above-referenced patent applications is the ability to mass-manufacture with plastic materials in continuous processes at a 1–2 feet/minute rate. Methods of mass production of the sensors are disclosed in U.S. Patent application publication 2003/0017581. As shown in FIG. 1, the periodic surface structure of a biosensor 10 is fabricated from a low refractive index material 12 that is overcoated with a thin film of higher refractive index material 14. The low refractive index material 12 is bonded to a substrate 16. The surface structure is replicated within a layer of cured epoxy 12 from a silicon-wafer "master" mold (i.e. a negative of the desired replicated structure) using a continuous-film process on a polyester substrate 16. The liquid epoxy 12 conforms to the shape of the master grating, and is subsequently cured by exposure to ultraviolet light. The cured epoxy 12 preferentially adheres to the polyester substrate sheet 16, and is peeled away from the silicon wafer. Sensor fabrication was completed by sputter deposition of 120 nm titanium oxide ($TiO_2$) high index of refraction material 14 on the cured epoxy 12 grating surface. Following titanium oxide deposition, 3×5-inch microplate sections are cut from the sensor sheet, and attached to the bottoms of bottomless 96-well and 384-well microtiter plates with epoxy.

As shown in FIG. 2, the wells 20 defining the wells of the mircotiter plate contain a liquid sample 22. The combination of the bottomless microplate and the biosensor structure 10 is collectively shown as biosensor apparatus 26. Using this approach, photonic crystal sensors are mass produced on a square-yardage basis at very low cost. The detection instrument for the photonic crystal biosensor is simple, inexpensive, low power, and robust. A schematic diagram of the system is shown in FIG. 2. In order to detect the reflected resonance, a white light source illuminates a ~1 mm diameter region of the sensor surface through a 100 micrometer diameter fiber optic 32 and a collimating lens 34 at nominally normal incidence through the bottom of the microplate. A detection fiber 36 is bundled with the illumination fiber 32 for gathering reflected light for analysis with a spectrometer 38. A series of 8 illumination/detection heads 40 are arranged in a linear fashion, so that reflection spectra are gathered from all 8 wells in a microplate column at once. See FIG. 3. The microplate+biosensor 10 sits upon a X-Y addressable motion stage (not shown in FIG. 2) so that each column of wells in the microplate can be addressed in sequence. The instrument measures all 96 wells in ~15 seconds, limited by the rate of the motion stage. Further details on the construction of the system of FIGS. 2 and 3 are set forth in the published U.S. Patent Application 2003/0059855. Preferred manufacturing methods for manufacturing biosensors are disclosed in the United States Provisional patent application of Stephen Schulz filed on the same date as this application, "An Optimized Grating Based Biosensor and Substrate Combination," Ser. No. 60/693,680.

All of the previously cited art is fully incorporated by reference herein.

SUMMARY

The following embodiments and aspects thereof are described and illustrated in conjunction with systems, tools and methods which are meant to be exemplary and illustrative, not limiting in scope. In various embodiments one or more of the above-described problems have been reduced or eliminated, while other embodiments are directed to other improvements.

A biosensor substrate structure is provided that eliminates the effects of optical interference of light reflected from a substrate/air interface with light reflected by the biosensor's active surface by incorporating a roughened or "non-specular" surface on the surface of the substrate opposite to the surface supporting the grating. One can generate a useful non-specular or "anti-interference" surface in a number of ways in accordance with this disclosure, including (1) by adding a coating of optically diffuse material, such as UV cured acrylate, to the sensor substrate, (2) etching or otherwise roughening the surface of the sensor substrate, or (3) applying a grating structure to the surface.

In one embodiment, a biosensor is described which is adapted to be illuminated by a light source for detection of a substance loaded onto the biosensor. The biosensor comprises a grating structure for containing a sample and a substrate material supporting the grating structure. The substrate material has a surface oriented in the direction of the light source, wherein the surface is treated so to as to provide a diffusive, roughened property to the surface.

In another embodiment, a biosensor detection system is provided comprising a light source, a biosensor adapted to be illuminated by the laser light source and a detector for detecting light reflecting from the biosensor. The biosensor comprises a grating structure for containing a sample, and a substrate material having a first surface supporting the grating structure and an opposite second surface, wherein the opposite second surface is treated so as to provide a diffusive, roughened property to the surface.

In still another embodiment, a method of manufacturing a biosensor is provided comprising the steps of: a) providing a substrate having an upper surface and a lower surface; b) applying a grating to an upper surface; and wherein the lower surface of the surface is treated to provide a diffusive, roughened property to the lower surface. As noted herein, several different treatments are possible to provide the diffusive, roughened property to the surface.

In one possible embodiment, the method is performed and the biosensors constructed on a substrate which has a coating applied to the substrate to thereby provide the treatment to the lower surface. The substrate is obtained in bulk from a manufacturer in which the coating has been applied to the substrate in previous manufacturing process. For example, it is possible to purchase from manufacturers PET film (the substrate material) pre-coated with a cured UV acrylate matte finish layer on one side (known in the art as an anti-glare hard coating). This embodiment is presently preferred, as it avoids the sensor manufacturer of having to take additional process steps to a base PET film to provide the treatment to roughen it.

BRIEF DESCRIPTION OF THE DRAWINGS

Exemplary embodiments are illustrated in referenced figures of the drawings. It is intended that the embodiments and figures disclosed herein are to be considered illustrative rather than restrictive

DETAILED DESCRIPTION

Several types of optical biosensors operate through the illumination of a biosensor device at angles of normal or near-normal incidence. Of particular importance are biosensors based upon photonic crystal concepts, such as guided mode resonance filter (GMR) biosensors described in the above-referenced patent applications or silver nanoparticle array biosensors. For these types of biosensors, the attachment or incorporation of biochemical material (such as DNA, RNA, chemical molecules, proteins, viruses, bacteria, or cells) to the active sensor surface modifies the sensor's reflection/transmission characteristic as a function of illuminating wavelength. Frequently, the active (grating) surface is supported by a substrate material, such as glass or plastic (e.g., PolyEthylene Terephthalate (PET), commonly known as Mylar TM) that enables integration of the biosensor into a system. The substrate typically has a planar structure with flat and parallel upper and lower surfaces. The biosensor active surface may be illuminated directly (from above) or through (from below) the substrate material. The illumination source may be a broadband source, such as a light bulb or light emitting diode (LED) that provides wavelengths over a wide range (100–1000 nm range for a light bulb, or 1–100 nm range for an LED). Alternatively the illumination source may be a narrowband source such as a laser (<1 nm range).

Figure 4:
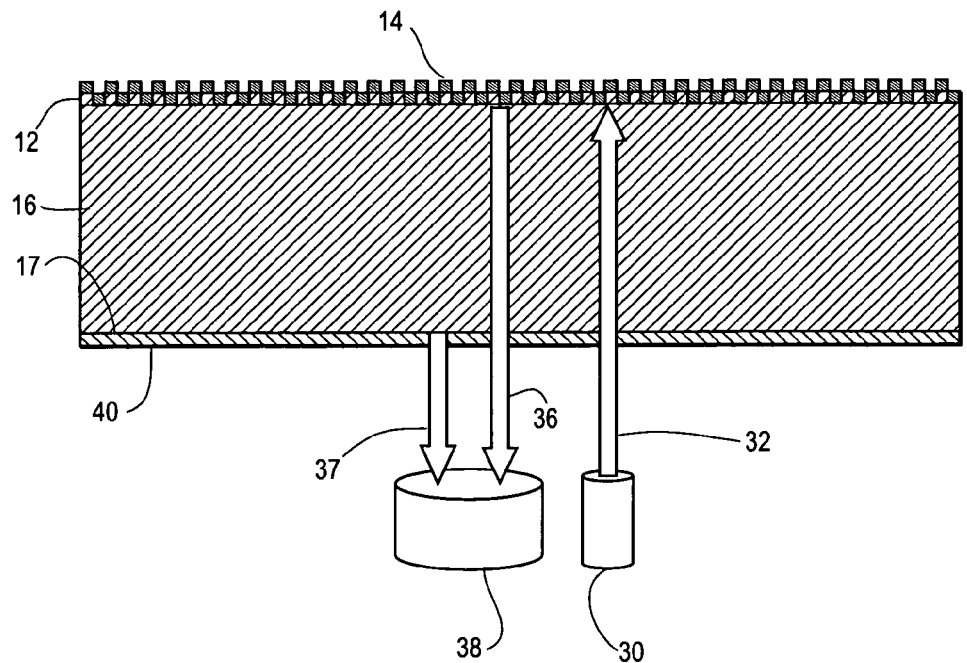
FIG. 4 is a cross-section of a biosensor in accordance with a preferred embodiment.

Referring to FIG. 4, a preferred embodiment of a biosensor is shown in cross section. The sensor includes a grating layer 12 applied to a substrate 16, which may be a PET film. High index of refraction material 14 is deposited on the grating layer 12. The lower surface 17 of the substrate has applied thereto an optically diffuse layer 40. The layer 40 may take the form of a matte coating (UV cured acrylate-based material), a roughening of the surface 17 or a grating applied to the surface 17. It is possible to purchase from manufacturers PET film pre-coated with a cured UV acrylate matte finish layer on one side (known in the art as an anti-glare hard coating). This embodiment is presently preferred, as it avoids the sensor manufacturer of having to take additional process steps to a base PET film to either roughen it or add the grating layer.

Figure 1:
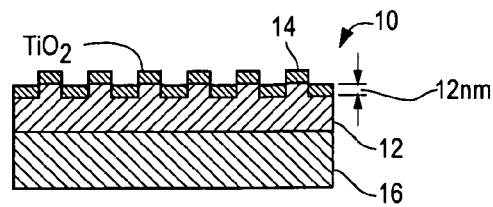
FIG. 1 is an illustration of a prior art biosensor arrangement.
Figure 2:
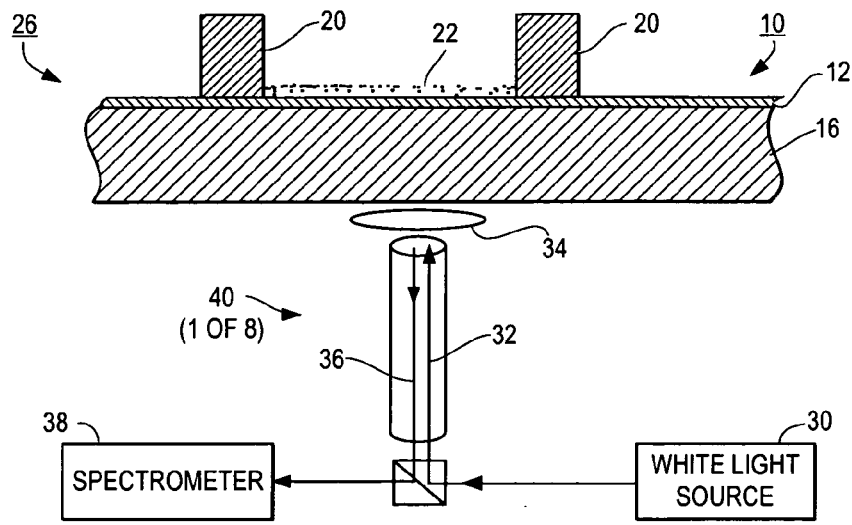
FIG. 2 is an illustration of a prior art biosensor and detection system for illuminating the biosensor and measuring shifts in the peak wavelength of reflected light from the biosensor.
Figure 3:
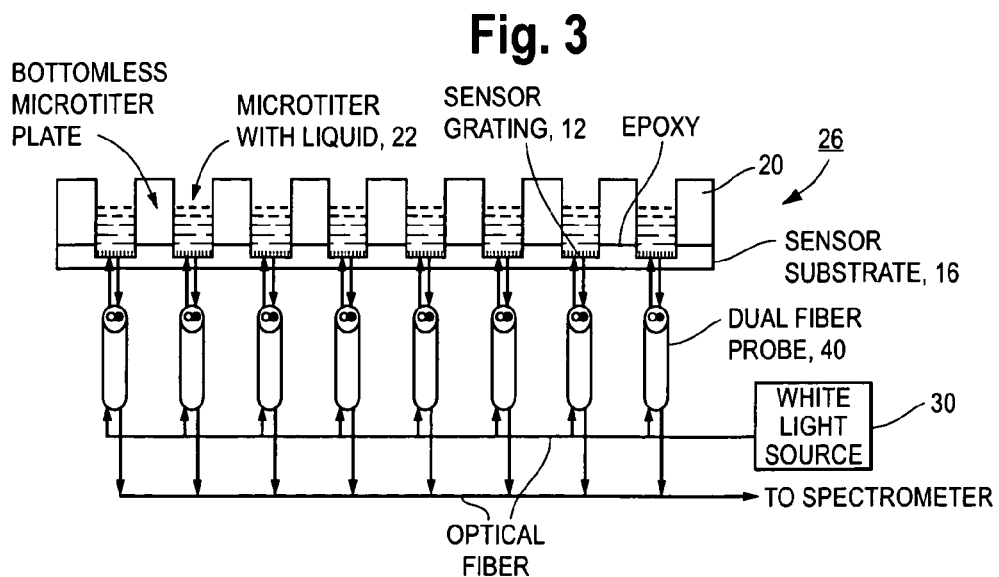
FIG. 3 is an illustration of an arrangement of 8 illumination heads that read an entire row of wells of a biosensor device comprising the structure of FIG. 1 affixed to the bottom of a bottomless microtiter plate.

The construction of FIG. 4 overcomes an optical interference problem that would otherwise occur without the usage of the layer 40, e.g., in the embodiment of FIGS. 1–3. In particular, any two optically distinct interfaces within the biosensor construct will generate an optical interference spectral pattern. Light waves reflecting from two interfaces and traveling in the same direction interfere constructively (when in-phase) or destructively (when out of phase). Constructive interference results in higher intensity. Destructive interference results in lower intensity. In the case of normal incidence, destructive interference occurs when $2nd=m\lambda/2$, where d represents the distance between interfering interfaces along the optical axis, $\lambda$ a particular wavelength, n the refractive index of the media between the interfaces, and m an integer. Constructive interference occurs when $2nd=m\lambda$. For fixed d and n, intensity will modulate, high and low, across a spectral range. Interference effects occur both with reflected light and transmitted light as well as with varying angle of incidence.

With continued reference to FIG. 4, this invention addresses, primarily, interference of light 37 reflected from the substrate/air interface (17) with light 36 reflected by the biosensor active surface. These surfaces 12 and 17 produce the largest reflected intensity, which results in the most significant interference effect. In addition, the relatively large substrate 16 thickness, causes interference maxima and minima to have close spectral spacing; spacing on the order of useful spectral features produced by the biosensor. This similarity of spectral periodicity, between the substrate interference and the biosensor information signal, increases sensor signal uncertainty.

Observation of the reflected or transmitted spectrum from the substrate-biosensor construct thus results in a periodic modulation of intensity as a function of wavelength superimposed upon the reflection or transmission characteristic of the active biosensor surface e.g. a sharp resonance peak. The period and position of the interference extrema depend upon subtle spatial variation of the substrate thickness as well as the wavelength of operation, and therefore the characteristics of the modulation are not completely predictable nor spatially uniform.

Referring again to FIG. 4, to address the problem, in a first aspect a substrate structure 16 is provided that eliminates the effects of optical interference by incorporating a roughened or "non-specular" surface 40 on the lower side of the substrate, which in this instance is opposite the biosensor's illumination and detection apparatus 30 and 38. Note that the invention does not require that the substrate lie between the grating the illumination apparatus. Illumination could occur from the grating side. As noted, one can generate a useful roughened surface 40 in a number of ways in accordance with this disclosure, including (1) by adding a coating of optically diffuse material to the substrate bottom surface 17 (or purchasing the substrate 16 from a supplier with the coating already applied), (2) by etching the surface 17 to form a roughened surface 40, or (3) by applying a grating structure to the surface 17.

The diffuse coating can, for example, consist of a relatively hard cross-linked polymer material containing transparent particles sized to yield an appropriate surface roughness.

Etch treatment of the substrate surface 17 may be performed, for example, in a plasma chamber. The resulting etching can produce a surface with finer features.

A grating, embossed or printed on the surface 17, can produce a similar effect. Methods of applying a grating to a sensor substrate are disclosed in the United States Provisional patent application of Stephen Schulz filed Jun. 23, 2005, "An Optimized Grating Based Biosensor and Substrate Combination," Ser. No. 60/693,680, the content of which is incorporated by reference herein. The additional lower surface grating acquires antireflective properties. This method of solving the interference problem, however, presently increases sensor cost prohibitively. However, this may be remedied as technology improves.

The patent literature, in the area of displays, touchscreens, or photographic reproduction, contains examples of similar surface treatments for elimination of "Newton rings". See e.g., U.S. Pat. Nos. 6,592,950 and 6,555,235. Newton rings refer to visible and spatially distributed interference patterns generated, for example, by a small air gap. "Anti Newton ring" (ANR) treatments or coatings destroy the coherence of light reflected from one or both surfaces comprising the air gap. In the case of a biosensor, the troublesome interference pattern arises from interference within the substrate rather than between two substrates. The interference fringes that occur within the biosensor substrate have much closer spectral spacing making them invisible to the eye but disruptive to sensor operation. The application of such ANR techniques to the field of optical biosensors is believed to be novel.

The layer 40 applied to the surface 17 of the substrate structure 16, as described herein, eliminates optical interference between the upper and lower surfaces of the substrate by preventing light reflected from this lower surface from aligning coherently with light reflected from an upper interface between the substrate 16 and the grating 12.

The invention is particularly useful for optical biosensors where measurement sensitivity depends on detecting small changes in the spectral distribution of the reflected or transmitted spectra. In this case, spectral modulation caused by interference, superimposed onto the biosensor optical signal, adds error and decreases sensor resolution.

The problem of interference in optical biosensors has been addressed in several different ways in the prior art, all with their own attendant disadvantages.

1. Boxcar Averaging

The optical interference effect can be mathematically removed from a biosensor reflectance or transmittance spectra by a technique called boxcar averaging. A reflectance or transmittance spectra is typically gathered over a wide range of wavelengths by a series of discreet measurements taken at small intervals. For any particular wavelength, $\lambda$, the next closest measurements in the spectra will be $\lambda + D\lambda$, and $\lambda - D\lambda$, where $D\lambda$ represents the wavelength interval, in practice determined by the spectrometer hardware. Boxcar averaging determines, for all $\lambda$, an averaged response and the neighboring responses over a specified interval, b, called the "boxcar length." The new, averaged spectra, $g(\lambda)$, can be calculated from the measured spectra, $f(\lambda)$, by the formula:

$$g(\lambda) = \frac{1}{2b+1} \sum_{n=-b}^{+b} (f(\lambda + n\Delta\lambda))$$

The boxcar average will provide a smoothed reflectance spectra by averaging the high and low portions of the spectra generated by the interference effect. This approach has some disadvantages. Primarily, the interference period cannot always be predicted given process variations during the manufacture of the biosensor. The actual use of the biosensor also changes the interference period. To achieve optimum results, one would need to analyze the spectrum for interference and then tune the boxcar average to the specific circumstance. Secondly, the averaged spectrum represents a "lower resolution" version of biosensor's optical response. The averaging process may obscure subtle shifts of the spectrum produced by binding of biochemical material. To effectively remove the spectral modulation induced by interference, one must average over a range that approximates the period of the interference, ideally more that one period. If the interference modulation has a period similar to important biosensor spectral features (e.g. resonance peak) then averaging can effectively flatten the biosensor's spectral response and limit detection of small response changes.

2. Antireflective Coating

Given that interference effects occur between light waves reflected from two surfaces, suppressing reflection from either surface diminishes interference. Hence, application of an antireflective (AR) coating to the substrate surface 17 opposite the biosensor optical components can diminish the superposition of interference modulation on the biosensor response. AR coatings reduce the reflected intensity from a boundary between two materials of differing refractive index over a predetermined "design" wavelength range. Typically, AR coatings consist of thin films of dielectric materials applied with high accuracy by processes such as evaporation or sputtering. The thickness, refractive index, and number of layers comprising a thin-film based AR coating determine its useful spectral width, location, and reflection level. Minimizing the reflected energy from the substrate-air interface on the surface opposite the active biosensor minimizes interference from light reflected by that surface.

Application of AR coatings adds considerable cost compared with the solution offered by this invention. Furthermore, staining or scratching the bottom surface of an AR coated biosensor produce renders the AR coating ineffective. The diffuse coatings employed by this invention have exceptional durability and can be obtained at low cost.

3. Use of Nonplanar Substrate

Optical interference between the front and back surfaces of a biosensor substrate can be reduced or eliminated if the front and back surface of the substrate are not parallel to each other. In this case, light reflected from the top and bottom surfaces of the substrate are not parallel to each other and do not have the opportunity to constructively and destructively interfere. This solution does not lend itself well to high volume manufacturing on bulk planar substrate material.

Functional Advantages

Using the teachings of this disclosure, a number of advantages are obtained:

1. Accuracy and simplicity in measuring small shifts in biosensor reflectance or transmittance characteristics is obtained as compared to boxcar averaging techniques.
2. The biosensor is well-suited for use in systems where the biosensor peak wavelength value is obtained by a laser—due to the higher likelihood for coherence.
3. Lower cost (~10×) compared to the cost of deposition of antireflective coatings on the sensor surface.
4. The solution allows for an implementation of a biosensor detection instrument that measures the biosensor by illuminating the sensor at normal, or near normal, angles of incidence. Normal or near normal is most convenient for simple and robust optical alignment of illumination source and detector.

EXAMPLE

Figure 5:
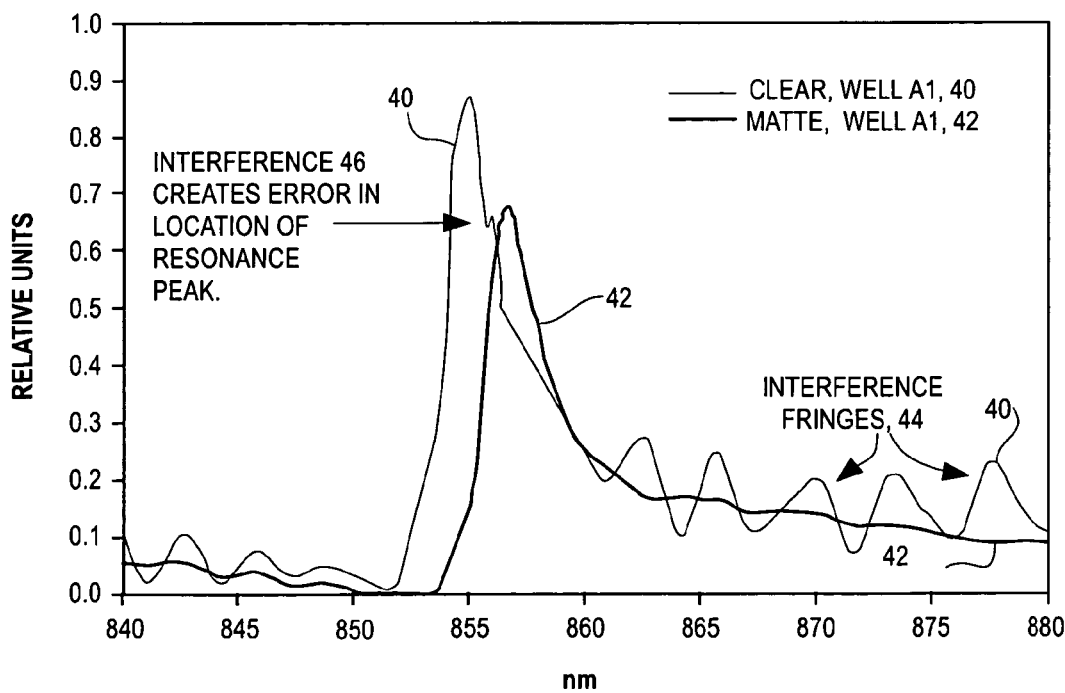
FIG. 5 shows two graphs of intensity as function of wavelength, with one graph for a sensor of the type shown in FIGS. 1–3 and the other for a sensor of the type shown in FIG. 4.

FIG. 5 shows two graphs of intensity as function of wavelength, with one graph represented by line 40 for a sensor of the type shown in FIGS. 1–3 and the other (line 42) for a sensor of the type shown in FIG. 4 with the layer 40 formed as a matte of cross-linked polymer acting as an optically diffuse layer. Note in FIG. 5 the interference between the reflected light from the biosensor active surface and the lower surface of the substrate creates a local maximum 46, and this maximum due to interference can create an error in the calculation of the location of the resonance peak. Note also the interference fringes 44 in the line 40. However, with the biosensor construction of FIG. 4, the line 42 does not have any interference fringes or local maxima (as in the case of 46) to skew or cause error in the calculation of the peak resonance frequency. Similar results would be expected for surface roughening of the layer 17 or by applying a grating to the lower surface 17 of the sensor substrate.

While a number of exemplary aspects and embodiments have been discussed above, those of skill in the art will recognize certain modifications, permutations, additions and sub-combinations thereof. It is therefore intended that the appended claims and claims hereafter introduced are interpreted to include all such modifications, permutations, additions and sub-combinations as are within their true spirit and scope.

We claim:

1. A biosensor adapted to be illuminated by a light source for detection of a substance loaded onto the biosensor, comprising:
   a grating structure for containing a sample, the grating structure reflecting light from the light source at a resonance peak in a narrow band of the spectrum; and
   a substrate material having a first surface supporting the grating structure, wherein the substrate material has an opposite second surface, wherein the opposite second surface is treated so to as to provide a diffusive, roughened property to the surface.

2. The biosensor of claim 1, wherein the treatment comprises applying a coating of an optically diffuse material to the second surface.

3. The biosensor of claim 2, wherein the coating comprises a UV cured acrylate.

4. The biosensor of claim 1, wherein treatment comprises etching the second surface.

5. The biosensor of claim 1, wherein the treatment comprises roughening the second surface.

6. The biosensor of claim 1, wherein the treatment comprises a coating applied onto the second surface containing a material roughening the second surface.

7. The biosensor of claim 6, wherein the coating comprises cross-linked polymer material containing transparent particles sized to yield a surface roughness.

8. The biosensor of claim 1, wherein the treatment comprises applying a grating structure to the second surface.

9. The biosensor of claim 8, wherein the grating structure is embossed on the second surface.

10. The biosensor of claim 8, wherein the grating structure is printed onto the second surface.

11. The biosensor of claim 1, wherein the light source comprises a laser.

12. A biosensor detection system comprising:
    a light source,
    a biosensor adapted to be illuminated by the light source;
    a detector for detecting light reflecting from the biosensor, wherein the biosensor comprises:
    a grating structure for containing a sample, the grating structure reflecting light from the light source at a resonance peak in a narrow band of the spectrum; and
    a substrate material having a first surface supporting the grating structure and an opposite second surface, wherein the second surface is treated so as to provide a diffusive, roughened property to the second surface.

13. The system of claim 12, wherein the treatment comprises applying a coating of an optically diffuse material to the second surface.

14. The system of claim 13, wherein the coating comprises a UV cured acrylate.

15. The system of claim 12, wherein the treatment comprises etching the second surface.

16. The system of claim 12, wherein the treatment comprises roughening the second surface.

17. The system of claim 12, wherein the treatment comprises a coating applied onto the second surface containing a material roughening the second surface.

18. The system of claim 17, wherein the coating comprises a cross-linked polymer material containing transparent particles sized to yield a surface roughness.

19. The system of claim 12, wherein the nonspecular property is provided by applying a grating structure to the second surface.

20. The system of claim 19, wherein the grating structure is embossed on the second surface.

21. The system of claim 19, wherein the grating structure is printed onto the second surface.

22. A method of manufacturing a biosensor, comprising the steps of:
    a) providing a substrate having an upper surface and a lower surface;
    b) applying a grating structure to the upper surface, the grating structure reflecting light from a light source at a resonance peak in a narrow band of the spectrum; and
    wherein the lower surface of the substrate is treated to provide a diffusive, roughened property to the lower surface.

23. The method of claim 22, wherein treatment comprises coating an optically diffuse material onto the lower surface.

24. The method of claim 23, wherein the coating comprises a UV cured acrylate.

25. The method of claim 22, wherein the treating comprises etching the lower surface.

26. The method of claim 22, wherein the treating comprises roughening the lower surface.

27. The method of claim 22, wherein the treating comprises applying a coating to the lower surface of a material which roughens the surface.

28. The method of claim 27, wherein the coating comprises a cross-linked polymer material containing transparent particles sized to yield a surface roughness.

29. The method of claim 22, wherein the treating comprises applying a grating structure to the lower surface.

30. The method of claim 29, wherein the grating structure is embossed on the lower surface.

31. The method of claim 29, wherein the grating structure is printed onto the lower surface.

32. The method of claim 22, wherein the method is performed on a substrate which has a coating applied to the lower substrate surface to thereby provide the treatment to the lower surface, the substrate obtained in bulk and having the coating applied to the substrate in previous manufacturing process.

* * * * *